US006383489B1

(12) United States Patent
Sehon et al.

(10) Patent No.: US 6,383,489 B1
(45) **Date of Patent: *May 7, 2002**

(54) INACTIVATION OF GRANULOCYTES IN THE TREATMENT OF ESTABLISHED ALLERGIC RESPONSES

(76) Inventors: Alec Sehon, 695 Academy Road, Winnipeg, Manitoba (CA), R3N 0E8; Soji Bitoh, 5-2-29, Matsushiro, Tsukuba city, Ibaraki 305 (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/641,977

(22) Filed: May 2, 1996

Related U.S. Application Data

(63) Continuation of application No. PCT/GB94/02396, filed on Nov. 2, 1994.

(30) Foreign Application Priority Data

Nov. 3, 1993 (GB) ............................................ 9322652
Mar. 8, 1994 (GB) ............................................ 9404409

(51) Int. Cl.[7] .................... A61K 39/385; A61K 39/395; A61K 39/38

(52) U.S. Cl. ................................ 424/193.1; 424/152.1; 424/153.1; 424/172.1; 424/184.1; 424/185.1; 530/403

(58) Field of Search ........................... 424/184.1, 185.1, 424/172.1, 193.1, 805, 810, 152.1, 153.1; 514/885; 530/403

(56) References Cited

U.S. PATENT DOCUMENTS

| | | | | |
|---|---|---|---|---|
| 4,261,973 | A | * | 4/1981 | Lee et al. |
| 4,732,863 | A | * | 3/1988 | Tomasi et al. |
| 5,126,131 | A | | 6/1992 | Dintzis et al. |
| 5,256,559 | A | * | 10/1993 | Maraganore et al. |
| 5,428,128 | A | * | 6/1995 | Mensi-Fattohi et al. |
| 5,478,806 | A | * | 12/1995 | Nho |
| 5,620,884 | A | * | 4/1997 | Shorr et al. |

FOREIGN PATENT DOCUMENTS

| | | |
|---|---|---|
| EP | 92 496579 | 7/1992 |
| FR | 782362156 | 3/1978 |
| GB | 912238959 | 6/1991 |
| WO | 92 11029 | 7/1992 |

OTHER PUBLICATIONS

Sehon, A. H. et al Dual Effects of Alergen–mPEG Conjugates, New Horizons in Allergy Immunotherapy, edited by Sehon et al., Plenum Press, Ny, Chapter 24, pp. 177–184, 1996.*

Wie et al. Int. Archs Allergy Appl. Immun. 64:84–99, 1981.*

Fundamentals of Immunology, Paul, W. E., Ed., Raven Press, New York, NY, pp. 870–871, 1989.*

Dictionary of Immunology, Rosen et al., Eds., Stockton Press, New York, NY, p. 158, 1989.*

Rotti, I. Essential Immunology, Sixth Edition, Blackwell Scientific Publications, Boston, MA, pp. 193–195, 1988.*

Weir, D. M. et al. Immunochemistry, vol. 1, Fourth Edition, Blackwell Scientific Publications, Boston, MA, pp. 31.4–31.5, 1986.*

Sehon, et al. *Chemical Abstracts*, 105(15) Abstract No. 131744 "The use of nonionic, water soluble polymers for the synthesis of tolerogenic conjugates of antigens".

Wie, et al, *International Archives of Allergy and Applied Immunology*, 64(1), 1981 pp 84–99 "Suppression of reaginic antibodies with modified allergens".

* cited by examiner

*Primary Examiner*—David Saunders
*Assistant Examiner*—Amy DeCloux
(74) *Attorney, Agent, or Firm*—Antonelli, Terry, Stout & Kraus, LLP

(57) ABSTRACT

This invention is based on the discovery that an essentially nonallergenic covalent conjugate of a model allergen, ovalbumin (OA), and monomethoxypolyethylenc glycol (mPEG) is capable of inactivating in vivo and ex vivo granulocytes sensitized with anti-OA IgE antibodies (Abs). As a result of the inactivation of the granulocytes, subsequent challenge with OA was not followed by degranulation and the consequent release of the mediators of anaphylaxis (vasoactive compounds) from the granules of these cells. These results, therefore, provide a basis for the treatment of symptoms of an already established immune response against an allergen or allergens.

20 Claims, 1 Drawing Sheet

INACTIVATION OF GRANULOCYTES IN THE TREATMENT OF ESTABLISHED ALLERGIC RESPONSES

This is a continuation (35 U.S.C. 120) of International Application No. PCT/GB94/02396, with an international filing date of Nov. 2, 1994, claiming priority (35 U.S.C. 119) to GB 9322652.0, filed Nov. 3, 1993 and GB 9404409.6, filed Mar. 8, 1994.

The present invention relates to materials and methods relating to cell control and cell suppression.

One of the greatest challenges is to devise strategies for the selective control of the activities of particular cells. For example, a strategy for the inactivation of harmful cell responses such as undesirable immune responses, as in the case of IgE-mediated allergies, auto-immune disease, rejection of transplants.

UK Patent No. 1578348 and U.S. Pat. No. 4261973 disclose that an antigen or allergen such as ovalbumin (OA), and the non-dialysable constituents of the aqueous extract of ragweed pollen and dog albumin, may be converted to a tolerogen by coupling it to an optimal number (n) of monomethoxypolyethylene glycol (mPEG) molecules. Injection of tolerogenic mPEG conjugates of these antigens/allergens into rats and mice, led to abrogation of the capacity of the mice to mount humoral antibody responses to those immunogenic molecules. Further, these patents describe the establishment in mice of an IgE antibody response by the injection of an allergen comprising dinitrophenylated ovalbumin (DNP-OA). The mice were then treated with an OA-PEG conjugate. It was shown that the administration of the OA-PEG conjugate into the sensitized mice resulted in a very marked decrease of the ability of the mice to mount an immune IgE antibody response not only to OA but also to DNP on subsequent challenge with DNP-OA.

Allergies are caused by a wide variety of substances eg pollens, foods, dust, chemicals collectively referred to hereafter as environmental allergens. Generally speaking allergens are antigens and the terms allergen and antigen may be used interchangeably in the context of this application, but the term allergen is particularly used to denote a type of antigen which induces the production of antibodies of isotype IgE (which mediate Type I allergies) in addition to antibodies of other isotypes as generated in response to common antigens.

UK Patent No. 2238959 followed on from the above work and disclosed that pre-treatment of a recipient with a tolerogen suppresses the immune response not only to the antigen incorporated in the tolerogen, but also to a conjugate of that antigen and at least one additional antigenic moiety which may be a hapten or another unrelated protein. For example, the patent discloses that injection of a tolerogenic mPEG conjugate of human IgG (ie, $HIgG(mPEG)_{25}$) into mice, prior to administration of conjugates of human IgG with either dinitrophenyl DNP or DNP-keyhole limpet haemocyanin (KLH) (ie, $DNP_7$-HIgG or $DNP_{23}$-KLH-HIgG), led to the abrogation of the capacity of the mice to mount humoral antibody responses to both human IgG and the conjugated moiety DNP or $DNP_{23}$-KLH. If, however, the mice pretolerised to HIgG by injection of $HIgG(mPEG)_{25}$ were injected with a non-covalent mixture of $DNP_{23}$-KLH and human IgG, the mice mounted normal humoral antibody responses to DNP and KLH, but remained suppressed to human IgG.

The above discussed art concerns the use of mPEG-allergen conjugates to suppress the initial development of an immune response to an antigen (eg human IgG) or allergen (eg OA). However, there is a real need for products and treatment methods which are directed to the control of an already established immune response and hence the alleviation of the associated clinical symptoms.

Certain cellular functions are controlled by the cell membrane with changes in cell activity being mediated by changes in the cell membrane. This will now be discussed in more detail and by way of example only, the discussion is in relation to granulocytes which are involved in the body's immune response to an allergen.

When an individual is exposed to an allergen which is recognised by that individual's immune system as being foreign, there will be proliferation of antibody-producing B cells including $B_\epsilon$ cells, ultimately resulting in the formation of IgE antibodies with specificities for the different epitopes presented by the allergen circulating in the blood stream. The Fc region of an IgE antibody (referred to as $Fc_\epsilon$) binds with high affinity to $Fc_\epsilon$ receptors specific for IgE located in the surface membrane of various types of granulocytes, e.g., mast cells in tissues and basophils in the blood. Typically a mast cell will have $300–600\times10^3$ receptors for the Fc tails of IgE antibodies. The occupation of these receptors by IgE antibodies via their Fc tails results in the production of a cell which is said to be sensitised. Thus the sensitised granulocytes, e.g., mast cells, are effectively coated by IgE antibodies bound to the cell by the interaction of their Fc tails with the cell surface $Fc_\epsilon$ receptors. The antigen-binding sites (the Fab arms) of the coating IgE antibodies project into the surrounding medium. Since the Fc tail does not substantially vary from one IgE antibody to another (it is said to be "common"), a granulocyte may be coated with IgE antibodies of differing specificities.

When the sensitised mast cells or basophils come into contact with a multivalent allergen (ie an allergen having multiple epitopes available for binding to IgE antibodies), the allergen is bound by the Fab regions of different IgE antibodies, each antibody recognizing (ie reacting) the appropriate epitope. This has the effect of cross-linking the Fc receptors of the sensitised cells by the allergen. This results in the destabilisation of the mast cell membranes, followed by degranulation of these cells with the release of vasoactive compounds, such as histamine and heparin from their granules.

SUMMARY OF THE INVENTION

The present applicants describe herein experiments which show that if an animal already producing IgE antibodies to an allergen is treated with a conjugate of mPEG and the allergen, granulocytes involved in IgE-mediated inflammation (ie granulocytes coated with IgE antibodies some of which having specificity for the allergen) are inactivated. Thus, a water-soluble covalent conjugate of an allergen with one or more non-immunogenic polymeric molecules (i.e., polymeric chains) can be used to alleviate the symptoms of an already established immune response against the allergen.

Figure 1:
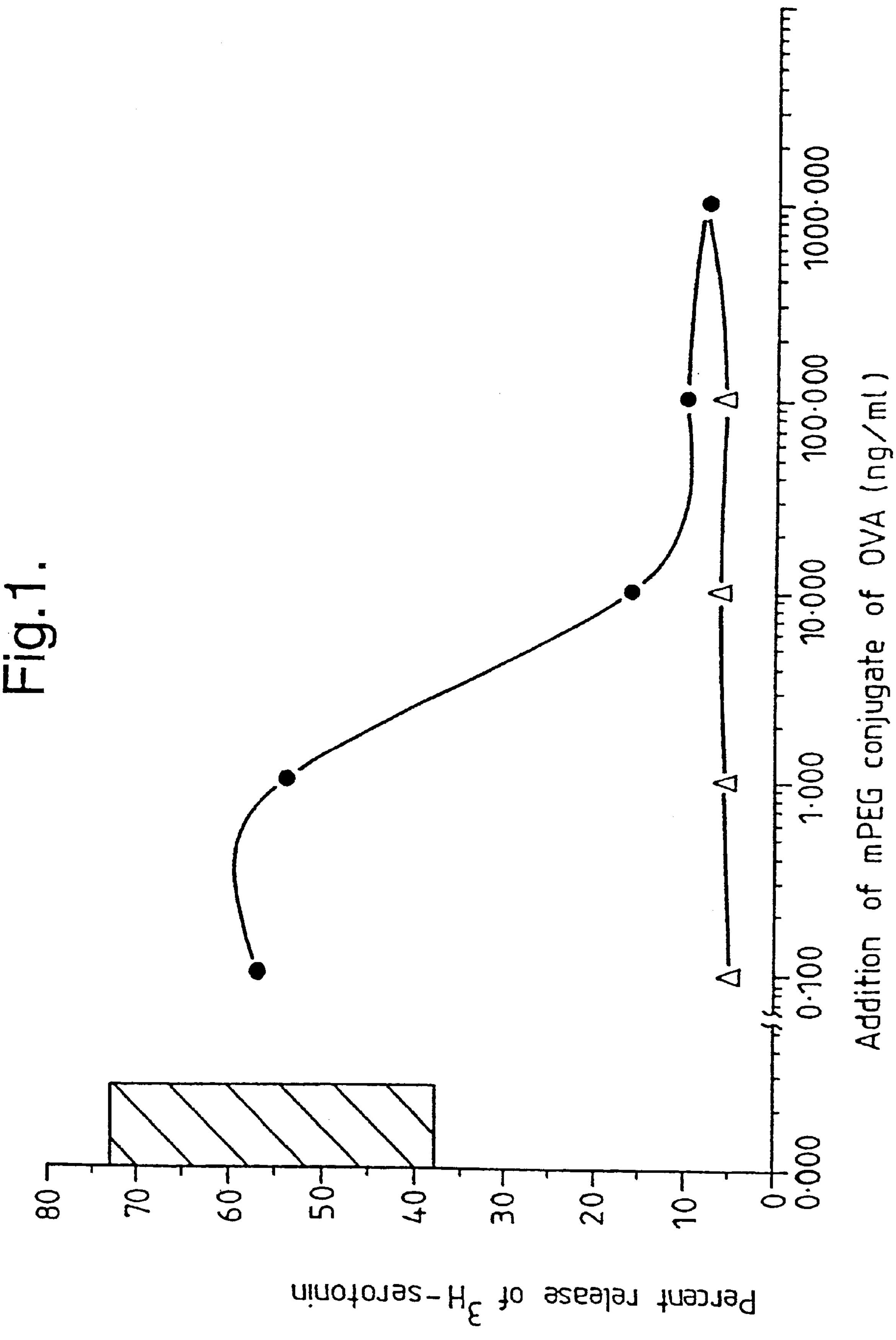
FIG. 1 is a graph showing the percent release of 3H-serotonin versus addition of mPEG conjugate of ovalbumin in in vitro experiments demonstrating the suppression of degranulation of sensitized mast cells by mPEG/ovalbumin.

The conjugation of mPEG to an allergen (eg OA) is thought to effectively mask most of the epitopes presented by the allergen. However, a few epitopes remain accessible for binding with IgE and other classes of immunoglobulins. If an IgE antibody with specificity for an accessible epitope of the allergen is fixed to the IgE receptor on the surface of sensitised granulocytes, this draws the mPEG-allergen conjugate close to the cell surface. However, because the number of unmasked allergen epitopes is greatly reduced, there is relatively little cross-linking, and insufficient for destabilisation of the cell membrane with consequent degranulation.

The applicants believe that when mPEG polymer chains are brought into close association with the surface membrane of a cell, they become either attached to, or intercalated with the cell membrane bilayer.

For example a conjugate of mPEG with an allergenic or antigenic epitope could be used to locate the mPEG chain onto the cell membrane of a B cell. For example, a conjugate of mPEG with an allergenic or antigenic epitope could be used to locate the mPEG chain onto the cell membrane of a B cell possessing surface immunoglobulins with Fab regions complementary to the given epitope. Although it may be visualised that the mPEG/antigen conjugate may be endocytosed, the mPEG may render the cell unable to intracellularly process the allergen or antigen, as the processing occurs by enzymatic digestion and no known enzyme has been shown to be capable of digesting the mPEG chain. Therefore endocytosis of a conjugate consisting of mPEG and a ligand (such as an antigen) for a cell would lead to impairment of the cell's intracellular digestion system i.e., constipation of the cell, which may be manifested by inactivation of the cell in question.

Whatever the precise mechanism eventually transpires to be (and it is not necessary to extensively hypothesise about the various mechanisms here), the present applicants teaching is that bringing mPEG into close association with a cell surface membrane by employment of a ligand for the membrane, can lead to cell inactivation or desensitisation.

In other words, the bringing of the mPEG chains into close association with a cell surface membrane leads to a signal which alters a particular cell function eg a negative signal may inhibit a particular cell function. This proposed mechanism is supported by the observation that mast cells sensitized with IgE antibodies to both ovalbumin and unrelated epitopes eg, the moiety dinitrophenyl (DNP), and then treated with an OA-mPEG conjugate fail to degranulate and release inflammatory mediators in response to challenge with either OA or a polyvalent dinitrophenylated protein such as $DNP_{15}$-BSA or $DNP_9$-OA (Tables 1 to 3). In particular, Table 3 illustrates that the treatment of mast cells with mPEG conjugated to a specific allergen, effectively prevents degranulation of the mast cells in response not only to the binding of the specific allergen comprised within the conjugate, but also to any other allergens for which the mast cell is carrying specific IgE antibodies simultaneously with the IgE antibodies to the allergen comprised within the mPEG conjugate.

Given the above, the applicants teach that provided a cell which one desires to control/alter the function of, has a suitable cell surface marker for which one is able to provide a ligand conjugated/complexed to mPEG, one may use the mPEG conjugate/complex (as the interaction between the cell surface marker and ligand draws mPEG into close proximity with the surface of the cell) as a medicament to control or alter a cell function which may be determined by the status of the cell surface membrane or mediated by changes in the cell surface membrane.

Thus the present invention provides use of a water soluble complex of (i) a ligand for a moiety on the surface of a target cell with (ii) one or more non-immunogenic polymers in the preparation of a medicament for administration to a patient in order to prevent or alleviate symptoms of a medical condition which symptoms are determined by an activity of the target cell which may be altered by the binding of the complex to the cell membrane of the target cell via an interaction between the ligand and cell surface moiety. The activity of the target cell may be determined by the structural and/or functional status of its cell membrane.

The target cell may be a cell involved in an immune response. The immune response may be against an allergen, a graft cell or tissue or the immune response may be an autoimmune response.

The target cell may be a phagocyte. Thus the target cell may be a granulocyte such as a mast cell or a basophil.

Alternatively, the target cell may be a lymphocyte. Thus the target cell may be a T-cell. The T-cell may be a cytotoxic T cell. Or the target cell may be a B cell.

The complex of ligand and non-immunogenic water-soluble polymer may be in the form of a covalent conjugate. Alternatively the complex may be formed through noncovalent associations. For example, the complex of ligand and non-immunogenic water-soluble polymer may be created by employment of the biotin-avidin system (or an equivalent system). The avidin may be bound to the ligand and the biotin may be bound to the non-immunogenic water-soluble polymer. The complex may be formed ex-vivo or in vivo. Thus where the complex is formed in vivo, the ligand as bound to avidin may be infused first for binding to the target cell. The non-immunogenic water-soluble polymer as bound to biotin may then be infused later and the binding of biotin and avidin will result in the formation of the complex, drawing the non-immunogenic water-soluble polymer onto the target cell surface and subsequently into the cell's endocytotic apparatus.

The cell-surface moiety may be a receptor or some other cell surface determinant. The cell-surface moiety may be an intrinsic part of the cell surface membrane structure. Alternatively it may be a molecule which, although not an intrinsic part of the cell surface membrane, is closely associated with the membrane. Thus the moiety may be part or all of an immunoglobulin which is fixed onto a particular cell (either naturally or by design). The moiety may be part or all of an immunoglobulin E.

Part or all of the complex may not be digestible by the cell for which the ligand has specificity. The water-soluble polymer may be selected from the group consisting of poly (alkylene-glycols), poly (vinyl alcohols), poly (vinyl pyrrolidones), poly (acrylamides), homo- and hetero-polymers of amino acids (including D amino acids), poly (saccharides), physiologically-acceptable derivatives, mixtures, combinations and functional equivalents thereof. The polymer may be poly (alkylene glycol) or its monomethoxy derivative. The polymer may be poly (ethylene glycol) or its monomethoxy derivative. Where the water-soluble polymer is poly (ethylene glycol) or its monomethoxy derivative, it may have a molecular weight in the range of 2,000–35,000. Preferably the molecular weight may be in the range of 3,000–6,000.

The ligand may comprise any molecule which has the capacity to bind to a cell surface moiety of the target cell. The ligand may be with or without the ability to cross-link/bridge those moieties. Thus the ligand may be monovalent, bivalent or multivalent. The ligand may comprise a molecule which comprises part or all of an immunoglobulin or an immunoglobulin-like binding domain. In particular, it may comprise part or all of the Fc tail of IgE. The ligand may comprise an allergen, or just one or more immunogenic epitopes of an allergen. As another example, it should also be mentioned that the activity of the target cell may under normal circumstances be affected/controlled by the binding or the absence of binding, of another complementary cell, the binding being via a system of complementary cell surface receptors and cell surface peptides. Thus the ligand for the surface of the target cell may comprise part or all of, or an analogue of part or all of the moiety (receptor or cell surface peptide) of the complementary cell which is complementary to a cell surface structure of the target cell.

Thus the invention as disclosed herein may-for example be applied to the inactivation of noxious cells e.g., cytotoxic T cells which are involved in an autoimmune response or which destroy a grafted organ, by administration of complexes of mPEG with part or all of an adhesion molecule e.g., of an endothelial molecule such as intercellular adhesion molecule-1, abbreviated to ICAM-1. ICAM-1 interacts with the antigen-nonspecific accessory molecule present on cytotoxic cells known as lymphocyte function associated antigen abbreviated to LFA-a1. LFA-a1 as well as extracellular matrix receptors may recognise ligands containing a core tripeptide of arginine-glycine-aspartic acid (RGD) or similar sequences. Hence the complex for inactivating target lymphocytes or other cells involved in, or responsible for inflammatory conditions may be of mPEG with a ligand in the form of a comparatively simple peptide sequence containing RGD or a functional equivalent.

Ligands may be reproduced by recombinant DNA methodologies. Of course, the ligand may not be specific for a cell surface moiety (such as an Fc receptor) which comprises an intrinsic part of the cell membrane, but it may have specificity for a cell surface moiety which although not an intrinsic part of the cell membrane itself, is closely associated with the cell membrane. A cell surface moiety which is artificially provided for association with the cell membrane may also be produced by recombinant DNA methodologies.

Thus where the medicament is targeted at granulocytes the ligand may comprise:

(i) a molecule which represents part or all of the Fc tail of an immunoglobulin of the IgE isotype;

(ii) an immunoglobulin-like binding domain with specificity for immunoglobulin of the IgE isotype (in which case the ligand binds to the IgE attached to the Fc receptors of the granulocyte cell surface specific for the Fc tail of IgE);

(iii) an immunoglobulin-like binding domain with specificity for the $Fc_\epsilon$ receptor on the cell surface;

(iv) an immunoglobulin-like binding domain with specificity for any cell surface marker characteristic of the granulocyte;

(v) an epitope as specifically recognised by immunoglobulin (eg IgE) fixed to the granulocyte cell surface (eg an allergen or an immunogenic epitope of an allergen)

As stated earlier, the ideas presented herein are not limited to granulocytes. There has already been a discussion of the general concept in relation to cytotoxic T cells. As another example, where one wants to control the activity of a B cell, the medicament may comprise a non-immunogenic water soluble covalent complex of mPEG with an epitope as specifically recognised by a complementary surface immunoglobulin on the B cell target. But of course any ligands with specificity for the B cell surface itself or some molecule closely associated with the B cell surface would suffice equally well and be in accordance with the generalised teaching herein.

In relation to B cells the applicants have demonstrated that administration of tolerogenic conjugates of protein antigens (HIgG and OA) and mPEG resulted in downregulation of antibody responses leading to B cell anergy in a T cell-independent and antigen-specific manner. The function of each of the tolerogenic conjugates of HIgG and OA, which was isolated with the homologous reverse immunosorbent, (ie the fraction of the conjugate which had retained B cell epitope(s) accessible to the homologous antibodies) induced antigen-specific anergy of naive B cells. These results are interpreted as indicating that anchoring of mPEG conjugates onto B cells, as a result of the primary interaction of their accessible epitopes with the cell membrane immunoglobulin, and the subsequent interaction of mPEG molecules with the membrane itself leads to the disruption of the cell's metabolism.

Furthermore, the teaching as provided herein should not be regarded as limited to cells of the immune system. Complexes as taught are thought to be useful for the controlling the function of any cell where the function which is determined by the status of the cell's surface membrane.

The complexes as taught are useful for making medicaments for preventing either partially or wholly the function of certain target cells, which function is determined by the state of the membrane of the target cell and involved in the manifestation of symptoms of a medical condition.

The present invention has particular applicability to the alleviation of the symptoms of an already established immune response against an allergen or allergens.

Thus the present invention provides use of a water soluble complex of (i) one or more non-immunogenic polymers with (ii) part or all of an allergen in the preparation of a medicament for the alleviation of granulocyte mediated symptoms of an existing immune response against an environmental allergen and wherein the allergen of said complex is able to bind with binding domains of IgE antibodies coating granulocytes involved in said immune response.

The allergen of the complex may be the same as, or different to the environmental allergen.

The part or all of an allergen in the water soluble complex may comprise only part or all of an immunogenic region of the allergen. The immunogenic region may comprise an epitope.

The present invention also provides use of a water soluble complex consisting of (i) one or more non-immunogenic polymers with (ii) a ligand in the preparation of a medicament for the alleviation of granulocyte-mediated symptoms due to an existing IgE antibody immune response against an environmental allergen or allergens and wherein the ligand is able to bind to cell surface moieties of granulocytes involved in said immune response. The ligand may bind to cell surface moieties of granulocytes in such a manner as to render binding dormains of IgE antibodies coating said granulocytes involved in said immune response unavailable for binding with said environmental allergen.

The ligand may comprise part or all of an antibody with specificity for the IgE antibodies coating the granulocytes involved in the immune response. The ligand may comprise an anti-idiotypic antibody.

Where an immune response is already established against an allergen it means that granulocytes are coated with IgE antibodies with specificity to the allergen in the complex and normally also with IgE antibodies with specificity to an allergen different from the allergen in the water soluble complex. In which case, the symptoms are those resulting from degranulation of the granulocytes and the release of vasoactive compounds from their granules. Hence the function of the complex is to reduce or prevent degranulation and hence to partially or completely inhibit the release of the vasoactive compounds from the granules, which compounds are responsible for the manifestation of the medical symptoms mediated by IgE.

Granulocytes may be basophils or mast cells.

The present invention also has particular applicability to the inactivation of cells of the immune system (phagocytes and lymphocytes as mentioned earlier) in order to restrict the body's immune response against an antigen which may be native to the body (ie an autoimmune response is occurring) or foreign to the body. In which case the water-soluble complex will comprise one or more non-immunogenic polymers and a ligand able to bind to cell surface moieties of the particular cells one is wanting to inactivate.

Thus where the cell is a T cell (which as an example, may be involved in an undesirable immune response against a graft of an organ or cells or against tissues or cells of the body as in an autoimmune response) the present invention provides use of a water-soluble complex of (i) one or more non-immunogenic polymers with (ii) a ligand for lymphocyte function associated antigen of a T-cell in the preparation of a medicament for the restriction of a T-cell response against an antigen.

The T cell may be a cytotoxic T cell.

The ligand may comprise the tripeptide arginine-glycine-aspartic acid (RGD) or any other core sequence of amino acids recognised by a lymphocyte function associated antigen. The ligand may comprise just a core sequence or a polypeptide comprising such a core sequence. Thus the ligand may be an adhesion molecule such as the intercellular adhesion molecule-1 (ICAM-1).

Where the cell is a B cell, the present invention provides use of a water-soluble complex of (i) one or more non-immunogenic polymers with (ii) a ligand for a cell surface moiety of a B cell in the preparation of a medicament for the restriction of a B-cell response against an antigen. Where the cell surface moiety is an antibody, the ligand may comprise an antigen able to bind therewith. In the alternative, the ligand may comprise part or all of an antibody with specificity for an antibody coating the B cell surface. The ligand may comprise an anti-idiotypic antibody.

The one or more non-immunogenic polymers may be as described above. Similarly the complex may be formed through covalent or non-covalent associations as described above.

The present invention also provides treatment methods employing the above described complexes/conjugates and medicaments.

In order that the present invention is clearly understood, embodiments will now be described by way of example only with reference to the following experimental results and embodiments in which FIG. 1 1 shows % release of tritiated serotonin from sensitized mast cells for two different treatment regimes.

1. Preparation of Conjugates Containing mPEG

Conjugates of allergens such OA with mPEG may be made for example, in accordance with the general teaching set out in UK Patent Nos. 1578348 and 2238959.

Generally speaking, the complexes of the present invention can be prepared in accordance with standard chemical coupling procedures known in the art. For example, the chemical reaction may be in accordance with the reaction below:

$$\text{mPEG-CH}_2\text{I+Ligand-[linker]-SH} \rightarrow \text{mPEG-CH}_2\text{—S-[ligand]-peptide}$$

This coupling procedure leads to the formation of stable thioether bonds. The linker is optional and may be a neutral tri- or tetra-peptide with a terminal cysteine.

2. Reduced Allergenicity of the $OA(mPEG)_{11}$ Conjugate with Respect to that of OA The applicants have previously reported that the coupling of an optimal number of monomethoxypolyethylene glycol (mPEG) molecules onto a protein antigen (Ag), eg, OA and HIgG, resulted not only in impairment of its antigenicity, but also in its conversion to a specific tolerogen with respect to the original Ag.

The applicants now show that mPEGylation of allergens resulted in marked reduction of their allergenicity as demonstrated by the Prausnitz-Kustner passive skin sensitization test (P-K test), utilising IgE antibodies of an already established immune response, In a P-K test, a small volume of serum containing IgE antibodies to one or more allergenic epitopes is injected intradermally into the skin of a normal recipient (usually the recipient is of the same species as that from which the serum derives). These IgE antibodies bind to granulocytes (ie mast cells) in the skin of the recipient via the $Fc_\epsilon$ receptors in the cell surface membrane. One or two days are allowed to lapse, so that the local skin irritation due to the injection disappears. Allergen(s) is then injected into the same site. Within 5 to 15 minutes one observes the formation of a wheal, this being a local inflammatory reaction due to the release of histamine and other vasoactive mediators of anaphylaxis from the granules of the granulocytes. Thus a P-K reaction essentially represents anaphylaxis limited to the site of injection of the serum containing IgE antibodies. Since the reaction is not easily discernible in rodent's skin, to make the inflammatory reaction readily visible, a dye such as Evans Blue dye in phosphate buffered saline (PBS) is injected into the recipient intravenously soon after injection with the challenge allergen. The dye then leaks into the site of inflammation which becomes blue.

The size of the wheal depends on (i) the number of IgE antibody molecules which become bound to the granulocytes at the injection site; this in turn depending on the concentration of IgE antibodies in the serum volume injected; and (ii) the dose of allergen used to challenge the sensitized site. The P-K titre is therefore defined as the reciprocal of the maximum dilution of serum which gives rise to a discernible skin reaction on challenge with the appropriate allergen. Normally this minimal reaction is taken as a hive of about 5 mm in diameter.

In the present study, skin sites on the backs of rats were sensitized with a 2-fold serially diluted pool of murine sera containing anti-OA IgE antibodies (hereinafter referred to as pooled serum; in order to raise the sera, the mice had been given multiple immunizing injections of 1 μg of OA adsorbed onto Al (OH) 3).

Forty eight hours later, each sensitized skin site was injected with 50 μg containing different doses of OA (100 ng and 1 μg) or of $OA(mPEG)_{11}$ (1 μg, 100 μg, 500 μg and 1 mg). The rats were then immediately given 1 ml of 1% Evans Blue solution in PBS intravenously. As is evident from the data given in Table 1, the P-K titer of the pooled serum was in the range of 320–640, when the skin sites were challenged with 100 ng to 1 μg of unmodified OA. In contrast, at least 100 $\mu$g of OA(mPEG)$_{11}$ was required to even induce a discernible P-K reaction and a dose greater than 500 $\mu$g of OA(mPEG)$_{11}$ was required to induce a P-K reaction equivalent to that induced by 100 ng of OA.

These results indicate that (i) mPEGylation of OA molecules resulted in the dramatic loss or impairment of its allergenicity, and (ii) the conjugate retained some allergenicity, ie the conjugate at a dose of 500 $\mu$g induced a P-K titer, but the titer was less than that induced by OA within the range of 100 ng to 1 $\mu$g.

3. Inhibition of Development of Passive Cutaneous Anaphylaxis (PCA) Reactions by Pretreament with OA(mPEG)$_{11}$ A PCA reaction consists essentially of the same features as a P-K reaction as described above. Thus skin sites are sensitized as described above for the P-K reaction. However the challenge antigen/allergen solution is then injected intravenously with dye (eg Evans Blue dye). This leads to the degranulation of mast cells and hence local inflammation in the sensitized site. The dye penetrates the site of inflammation and the blue-ing reaction is the PCA.

In recent unpublished experiments, the applicants have shown that treatment of naive mice with tolerogenic antigen-(mPEG)$_n$ conjugates led to anergy of naive B cells in an antigen-specific manner. Therefore, the experiments described below were designed to establish if these conjugates could also inactivate mast cells which had been sensitized with IgE antibodies to the corresponding antigens. For this purpose, sites of rat skin were sensitized with the serially diluted pooled serum. Twenty-four, 36 or 47 hours later, each of the sites were injected with 1 or 10 $\mu$g of the conjugate, or PBS, and 48 hours later, the rats were challenged with 1 mg of OA for induction of PCA reactions. The results given in Table 2 demonstrate that the PCA titer of the pooled serum was in the range of 320–640 (line 1), and that the PCA titer was not affected by injection of PBS (line 2). However, injection of the conjugate at a dose of 1 $\mu$g per site resulted in marked inhibition of PCA reactions (line 3) and a dose of 10 $\mu$g of the conjugate sufficed to induce almost complete suppression of PCA reactions (line 4).

These results show that treatment of sensitized skin mast cells with the tolerogenic conjugate resulted in prevention of the PCA reactions normally induced by subsequent treatment with unmodified OA. Similar results have been obtained with mPEG conjugates of saporin.

4. Suppression of Degranulation of Sensitized Mast cells by OA (mPEG)$_{11}$

In order to confirm the above in vivo results, the following in vitro experiments were performed. Rat mast cells of the 2H3 line were sensitized with 10 $\mu$g/ml of partially purified mouse anti-OA IgE antibodies in the presence of $^3$H-serotonin ($^3$H-5HT) and then washed. The mast cells were incubated for 30 minutes with OA (1 $\mu$g/ml) to induce degranulation. No release of $^3$H-5HT from sensitized mast cells was detected without addition of OA. To establish the effect of pretreatment of mast cells with OA(mPEG)$_{11}$, the conjugate was added to the cell culture for one hour; the cells were then washed thrice and the culture was continued with OA for 30 minutes. The results are shown in FIG. 1. The shaded area represents the range of release of $^3$H-5HT from the sensitized cells on addition of OA only. The filled circles indicate the percent release of $^3$H-5HT from cells that had been incubated for one hour with OA(mPEG)$_{11}$ at different concentrations, prior to treatment with OA for 30 minutes. The triangles represent percent release of $^3$H-5HT from sensitized mast cells by 100 pg/ml—1 $\mu$g/ml of OA(mPEG)$_{11}$ without addition of OA.

Thus the lower line of the figure (open triangles) represents % release of $^3$H-serotonin from mast cells presensitized in vitro with anti-OA IgE antibodies, on exposure to (ie on challenge with) OA(mPEG)$_{11}$ at different concentrations and in the absence of OA. Thus this lower line indicates that OA(mPEG)$_{11}$ is essentially non-allergenic (ie not able to cross-link in the anti-OA IgE antibodies on the mast cells and so induce degranulation) over the wide range of concentrations tested.

In contrast, the upper sigmoidal curve (filled circles) indicates that the release of $^3$H-serotonin by OA is inhibited by pretreatment of the sensitized cells with OA(mPEG)$_{11}$ over the concentration range of OA(mPEG)$_{11}$ shown on the X axis.

These in vitro results strongly support the conclusion that treatment of sensitized mast cells with the mPEG conjugate of the appropriate allergen prevents their degranulation by the corresponding allergen.

5. The Inhibition of Degranulation by Conjugate of an Unrelated Allergen

The experiments described above were carried out with OA and its mPEG conjugate. However, as is well known, allergic patients produce IgE antibodies to various components present in a given allergenic molecule eg, each allergenic component of a pollen is not necessarily covalently bound to the other components. Hence, it is important to establish if mPEG conjugates of one allergenic component could inhibit the degranulation induced by the other components present in the same allergenic mosaic.

With a view to exploring this possibility, skin sites of rats were sensitized with a mixture of the pooled serum and anti-DNP IgE mAb. Twenty-four hours later, each sensitized site was injected with 1 $\mu$g of the conjugate or PBS, and after an interval of 24 hours the rats were challenged intravenously with OA, DNP$_{15}$-BSA, or DNP$_9$-OA to induce PCA reactions. As shown in Table 3, in agreement with the results listed in Table 2, the injection of PBS did not affect development of PCA reactions induced by any of three antigens (ie OA, DNP$_6$-BSA and DNP$_9$-OA). The injection of OA(mPEG)$_{11}$ before challenge resulted in inhibition of PCA reactions which would be induced by OA (lines 2–4). Moreover, pre-injection of the conjugate also suppressed the PCA reactions on challenge with DNP$_6$-BSA (lines 5, 6) or with DNP$_9$-OA (lines 9, 10 and 11) in sites sensitized with relatively higher concentrations of anti-OA IgE monoclonal antibody as compared to anti-DNP IgE monoclonal antibody. However, this suppression was not observed in the sites which had been sensitized with relatively higher amounts of anti-DNP IgE mAb (lines 7, 12), or with only anti-DNP IgE mAb (lines 8, 13).

Hence, extrapolating from the above results, it may be inferred that treatment of allergic animals or humans with mPEG conjugates of a single allergen or immunodominant epitope thereof may suppress allergic symptoms due to a mosaic of allergenic components comprising the allergenic molecule.

6. Inactivation of B cells of Naive Mice (not primed mice) by Ag(mPEG)$_n$ Conjugates in the Absence of CD8$^{30}$ Suppressor T Cells The results are shown in Table 4.

Ag(mPEG)$_n$ conjugates were passed over an immunosorbent consisting of antibodies to the antigen in the conjugate. This resulted in two conjugate fractions, FrI comprising conjugate in effluent (effluent conjugate) and FrII comprising conjugate in eluate (eluate conjugate) (mild elution conditions). The FrII eluate conjugate represented about 5% of total Ag(mPEG)$_n$ conjugate and since this conjugate bound to the immobilised antibody, the antigen must be conjugated with mPEG in such a way that B cell epitopes of the antigen (ie determinants) were accessible for binding to the immobilised antibodies.

This FrII eluate conjugate induced highly significant suppression of antibody formation to the specific antigen, in mice depleted of $CD8^+$ T cells ($CD8^-$ mice). This depletion of $CD8^+$ T cells was achieved by 3 injections of anti-$CD8^+$ monoclonal antibodies given at 14, 15 and 16 days prior to immunizing the animals on day 0 and again on day 28. The purpose of the depletion of $CD8^+$ T cells was to rule out the possibility that the antibody suppression might have been due to activation of $CD8^+$ suppressor T cells, rather than directly to inactivation of the appropriate B cells. The anti-Ag antibodies were determined on day 42.

With reference to Table 4 it is interesting to note that unfractionated Ag(mPEG)$_n$ conjugates (ie not subjected to passage over the immunosorbent) induced only a minor suppression of anti-Ag antibodies (in the order of 10 to 15%), as compared with antibody titres in control mice which received PBS in lieu of conjugates.

In contrast, FrII eluate conjugate induced a suppression of antibodies in the order of 90%. On the other hand FrI effluent conjugate had, if anything, a slightly enhancing effect in relation to antibody formation. Hence, the minor suppression observed on pretreating the mice with the whole Ag(mPEG)$_n$ preparation may be attributable to the FrII eluate conjugate being present in the preparation contains.

In summary, as demonstrated in the applicant's earlier studies, mPEGylation of allergens results not only in reduction of their immunogenicity, but also in impairment of their allergenicity. Moreover, coupling of an optimal number of mPEG molecules onto allergens results in their conversion to tolerogenic derivatives.

The present specification describes experiments using ovalbumin (OA) as a model allergen in mice, which establish that:

(i) although, on an equal protein basis, the allergenicity of the tolerogenic mPEG conjugate OA(mPEG)$_{11}$ was 100–500 fold lower than that of the unmodified OA, injection of this conjugate into skin sites of rats, which had been sensitized with murine anti-OA IgE antibodies, resulted in prevention of the development of passive cutaneous anaphylaxis (PCA) reactions when the animals were challenged intravenously with OA 48 hours later;

(ii) inhibition of PCA reactions was not observed when only unrelated IgE antibodies, eg, anti-DNP IgE mAb, had been used for sensitization;

(iii) the development of PCA reactions in sites sensitized with a mixture of anti-OA and anti-DNP IgE antibodies was suppressed on condition that the mixture did not contain a disproportionately larger amount of anti-DNP IgE antibodies;

(iv) most importantly, treatment of sensitized mice with the conjugate (by i.v. injection or by inhalation) inhibited systemic anaphylaxis. On the basis of these results it may be envisaged that also mPEG conjugates of B and/or T cell epitopes of allergens may inactivate the corresponding B and/or T cells, as well as the mast cells and granulocytes carrying antibodies specific to the appropriate B cell epitopes.

These results demonstrate that treatment of mammals, which produce IgE antibodies (among other isotypes) to a given allergen, with tolerogenic mPEG conjugates of the appropriate allergen results in inactivation of the cells involved in IgE-mediated inflammation, including IgE-sensitized mast cells. Moreover, considering also the fact that these conjugates were essentially devoid of allergenicity and that mPEG conjugates of different proteins, including allergens, have been shown in many systems to be safe products in man, these results indicate the potential therapeutic usage of mPEG conjugates of allergens for inhibition of the effector phase of IgE-mediated allergies.

TABLE 1

LOW ALLERGENICITY OF OA(mPEG)$_{11}$ IN PRAUSNITZ-KÜSTNER REACTIONS

| Dose injected into sensitized site | Prausnitz-Küstner titers in three rats | | |
|---|---|---|---|
| OA | | | |
| 100 ng/site | 320 | 320 | 640 |
| 1 µg/site | 320 | 640 | 640 |
| OA(mPEG)$_{11}$ | | | |
| 1 µg/site | <10 | <10 | <10 |
| 10 µg/site | <10 | <10 | <10 |
| 100 µg/site | <10 | 20 | <10 |
| 500 µg/site | 160 | 320 | 640 |
| 1 mg/site | 640 | 640 | 1280 |

Each skin site on the back of 3 SD rats was sensitized with 100 µl of the pooled antiserum, which contained anti-OA IgE antibodies. Forty eight hours later, 50 µl of the indicated dose of OA or OA(mPEG)$_{11}$ was injected into the same sites and the rats were immediately injected i.v. with 1 ml of 1% Evans blue solution in PBS.

TABLE 2

INHIBITORY EFFECT OF OA(mPEG)$_{11}$ ON THE DEVELOPMENT OF PCA REACTIONS

| Injection of sensitized site | PCA titers of individual rats 24 hr | 36 hr | 47 hr |
|---|---|---|---|
| None | 320, 640, 320 | | |
| PBS | 320, 640, 320 | 320, 640, 320 | 320, 640, 640 |
| OA(mPEG)$_{11}$ 1 µg/site | 80, 40, 20 | 80, 20, 40 | 40, 20, 20 |
| OA(mPEG)$_{11}$ 10 µg/site | <10, 20, <10 | <10, 20, <10 | <10, <10, <10 |

Skin sites on the back of nine SD rats were sensitized intradermally with 100 µg of 2-fold serially diluted pooled antiserum [10 - 1,280], which contained anti-OA IgE antibodies. Twenty four, 36 and 47 hours later, 50 µl containing either (i) PBS (ii) 1 µg OA(mPEG)$_{11}$ or (iii) 10 µg OA(mPEG)$_{11}$ was injected into each site. Forty eight hours after sensitization, each rat was given 1 mg of OA solution supplemented with Evans blue. The results represents individual PCA titers of three rats.

TABLE 3

Inhibition of development of PCA reactions to unrelated allergen by OA(mPEG)$_{11}$

| Mixture of IgE Abs to OA and DNP | Ag used for challenge | PCA Reactions None | PBS | OA(mPEG)$_{11}$ |
|---|---|---|---|---|
| 1/320:NIL | OA | + | + | − |
| 1/320:1/1,280 | | + | + | − |
| 1/320:1/640 | | + | + | − |
| 1/320:1/320 | | + | + | − |
| 1/320:1/1,280 | DNP$_{15}$-BSA | + | + | − |
| 1/320:1/640 | | + | + | − |
| 1/320:1/320 | | + | + | ± |
| NIL:1/160 | | + | + | + |
| 1/320:NIL | DNP$_9$-OA | + | + | − |
| 1/320:1/1,280 | | + | + | − |
| 1/320:1/640 | | + | + | − |

TABLE 3-continued

Inhibition of development of PCA reactions to unrelated allergen by $OA(mPEG)_{11}$

| Mixture of IgE Abs | Ag used | PCA Reactions | | |
|---|---|---|---|---|
| to OA and DNP | for challenge | None | PBS | $OA(mPEG)_{11}$ |
| 1/320:1/320 | | + | + | + |
| NIL:1/160 | | + | + | + |

Each skin site on backs of three SD rats was sensitized with 100 μl of a mixture of the pooled antiserum, containing anti-OA IgE antibodies, and the supernatant of the culture of clone 26.82 producing anti-DNP monoclonal Ab (mAb) IgE; the final dilutions of the antiserum and of the culture supernatant are indicated in the first column. Twenty four hours later, 1 μg of $OA(mPEG)_{11}$ in 50 μl of PBS, or PBS alone, was injected into skin sites as indicated above the respective columns. After a further interval of 24 hours, each rat was given an i.v. injection of 1 mg of OA, or of $DNP_{15}$-BSA, or of $DNP_9$-OA with 1% Evans blue solution in PBS. The symbols (+), (−) and (±) refer, respectively, to PCA reactions, exceeding 5 mm in diameter, no detectable PCA reactions, and faint reactions.

TABLE 4

B CELL ANERGY INDUCED BY Ag (mPEG) CONJUGATES POSSESSING RESIDUAL CAPACITY TO BIND TO ANTIBODIES (ie BY CONJUGATES POSSESSING ACCESSIBLE B CELL EPITOPES)

| $CD8^-$ mice [a] | | | |
|---|---|---|---|
| Treatment [b] | Immunization [c] | IgG1 ELISA titers on day 42 | |
| on day 0 | on days 0 and 28 | anti-HIgG | anti-OA |
| PBS | $DNP_9$-HIgG | 11,850 (1.3) | N/A |
| $HIgG(mPEG)_{30}$ | " | 9,800 (1.3) | N/A |
| $HIgG(mPEG)_{30}$-Fr.I | " | 12,450 (1.4) | N/A |
| $HIgG(mPEG)_{30}$-Fr.II | " | 1,420 (1.3) | N/A |
| PBS | $DNP_9$-OA | N/A | 20,450 (1.3) |
| $OA(mPEG)_{10}$ | " | N/A | 16,890 (1.4) |
| $OA(mPEG)_{10}$-Fr. I | " | N/A | 21,460 (1.3) |
| $OA(mPEG)_{10}$-Fr. II | " | N/A | 2,570 (1.2) |

[a] BALB/c mice were given three daily i.p injections of anti-CD8 mAb (1 μg/day) on days -16, -15, -14 in order to deplete these mice of $CD8^+$ T cells; hence the mice were designated as $CD8^-$ mice.
[b] Each $CD8^-$ mouse of a group of 8 received i.p. on day 0 PBS, or 5 μg of unfractionated $HIgG(mPEG)_{30}$, or 5 μg of Fr.I or Fr.II of this conjugate, or 4.5 μg of unfractionated $OA(mPEG)_{10}$, or 4.5 μg of Fr.I or of Fr.II of this conjugate.
[c] For immunization all mice received i.p. 100 μg of $DNP_9$-HIgG or of $DNP_9$-OA on days 7 and 28, and their IgGi, antibodies to HIgG and OA were determined on day 42.

We claim:

1. A method of treating patients with the symptoms of release of vasoactive compounds from granulocytes in an already established immune response to an allergen by administering to the patient a water soluble complex of (1) at least one non-immunogenic water-soluble polymer, wherein the at least one non-immunogenic water-soluble polymer is a monomethoxy poly(alkylene glycol), and (2) a monovalent ligand that binds to IgE on granulocytes, wherein the monovalent ligand is different or immunologically distinct from the allergen causing the symptoms in the patient, whereby the water-soluble complex inactivates the granulocytes.

2. A method according to claim 1, wherein the complex is formed through covalent associations.

3. A method according to claim 1, wherein the polymer is monomethoxypolyethylene glycol (mPEG).

4. A method according to claim 1, wherein the polymer has a molecular weight in the range of 2,000–35,000.

5. A method according to claim 1, wherein the vasoactive compound is selected from the group consisting of histamine and serotonin.

6. A method according to claim 1, wherein the polymer has a molecular weight in the range of 3,000–6,000.

7. A method of treating patients with the symptoms of release of vasoactive compounds from granulocytes in an already established immune response to an allergen by administering to the patient a water soluble complex of (1) at least one non-immunogenic water-soluble polymer, wherein the at least one non-immunogenic water-soluble polymer is a monomethoxy poly(alkylene glycol), and (2) a monovalent ligand that binds to IgE on granulocytes, wherein the complex is formed through non-covalent associations, whereby the water-soluble complex inactivates the granulocytes.

8. A method according to claim 7, wherein the monovalent ligand is the same as or immunologically cross-reactive with an epitope of the allergen causing the symptoms in the patient.

9. A method according to claim 7, wherein the ligand is different or immunologically distinct from the allergen causing the symptoms in the patient.

10. A method according to claim 7, wherein the polymer is monomethoxypolyethylene glycol (mPEG).

11. A method according to claim 7, wherein the polymer has a molecular weight in the range of 2,000–35,000.

12. A method according to claim 7, wherein the polymer has a molecular weight in the range of 3,000–6,000.

13. A method according to claim 7, wherein the vasoactive compound is selected from the group consisting of histamine and serotonin.

14. A method of treating a patient with symptoms of release of vasoactive compounds from mast cells or basophils in an already established immune response to an allergen, the method comprising:

administering to the patient, a water-soluble complex of (1) at least one non-immunogenic water-soluble polymer, wherein the at least one non-immunogenic water-soluble polymer is a monomethoxy poly (alkylene glycol), and (2) a ligand, wherein the ligand consists of a monovalent Fab or Fv domain of an antibody directed to an epitope specific for IgE, whereby the complex binds to IgE that is attached to mast cells or basophils in the patient, whereby the complex inactivates said mast cells or basophils by stopping degranulation and release of vasoactive compounds.

15. A method according to claim 14, wherein the polymer is monomethoxypolyethylene glycol (mPEG).

16. A method according to claim 15, wherein the polymer has a molecular weight in the range of 2,000–35,000.

17. A method according to claim 15, wherein the polymer has a molecular weight in the range of 3,000–6,000.

18. A method according to claim 14, wherein the vasoactive compound is selected from the group consisting of histamine, and serotonin.

19. A method of inhibiting degranulation of granulocytes, comprising administering an effective amount of a conjugate of a water-soluble complex of one or more non-immunogenic water-soluble polymers, wherein the one or more non-immunogenic water-soluble polymer is a monomethoxy poly(alkylene glycol) and a ligand specific for IgE, which binds to said granulocytes whereby the water soluble complex inactivates the granulocytes, thereby inhibiting the degranulation of the granulocytes.

20. A method according to claim 19, wherein said one or more non-immunogenic water soluble molecule is monomethoxypolyethylene glycol.

* * * * *